(12) United States Patent
Arnone et al.

(10) Patent No.: US 11,389,394 B2
(45) Date of Patent: Jul. 19, 2022

(54) BUSINESS METHODS, PROCESSES AND SYSTEMS FOR COLLECTION, CRYOGENIC STORAGE AND DISTRIBUTION OF COSMETIC FORMULATIONS FROM AN OBTAINED STEM CELL BASED BIOLOGICAL MATERIAL

(75) Inventors: John S. Arnone, Shrewsbury, NJ (US); Burt Ensley, Sedona, AZ (US)

(73) Assignees: John Arnone, Shrewsberry, NJ (US); Ensley Burt, Sedona, AZ (US)

( * ) Notice: Subject to any disclaimer, the term of this patent is extended or adjusted under 35 U.S.C. 154(b) by 0 days.

(21) Appl. No.: 14/008,024

(22) PCT Filed: Mar. 27, 2012

(86) PCT No.: PCT/US2012/030774
§ 371 (c)(1),
(2), (4) Date: Dec. 9, 2013

(87) PCT Pub. No.: WO2012/135237
PCT Pub. Date: Oct. 4, 2012

(65) Prior Publication Data
US 2014/0140950 A1    May 22, 2014

Related U.S. Application Data

(60) Provisional application No. 61/588,841, filed on Jan. 20, 2012, provisional application No. 61/582,026, filed on Dec. 30, 2011, provisional application No. 61/468,132, filed on Mar. 28, 2011.

(51) Int. Cl.
| | | |
|---|---|---|
| *A61K 8/98* | (2006.01) | |
| *G06Q 50/10* | (2012.01) | |
| *G16H 10/40* | (2018.01) | |
| *A61K 8/64* | (2006.01) | |
| *A61Q 19/00* | (2006.01) | |

(52) U.S. Cl.
CPC ............ *A61K 8/981* (2013.01); *A61K 8/64* (2013.01); *A61Q 19/00* (2013.01); *G06Q 50/10* (2013.01); *G16H 10/40* (2018.01); *A61K 2800/10* (2013.01); *A61K 2800/84* (2013.01)

(58) Field of Classification Search
CPC ............ A61Q 19/00; A61K 2800/84; A61K 2800/10; A61K 8/64; A61K 8/981; G06Q 50/10; G16H 10/40
See application file for complete search history.

(56) References Cited

U.S. PATENT DOCUMENTS

| | | | | |
|---|---|---|---|---|
| 5,726,040 A | * | 3/1998 | Ensley | A61K 8/64 424/401 |
| 2005/0250202 A1 | * | 11/2005 | March | C12N 5/0653 435/366 |
| 2005/0260175 A1 | * | 11/2005 | Hedrick | A61B 17/00 424/93.7 |
| 2007/0082394 A1 | * | 4/2007 | Moscatello | C12N 5/0663 435/325 |
| 2013/0325492 A1 | * | 12/2013 | Dudzinski | G06Q 10/08 705/2 |

* cited by examiner

*Primary Examiner* — Blaine Lankford
(74) *Attorney, Agent, or Firm* — Dilworth & Barrese, LLP

(57) ABSTRACT

Business methods, processes and systems for collection, storage and distribution of a biological sample material for producing a cosmetic formulation product.

4 Claims, 3 Drawing Sheets

BUSINESS METHODS, PROCESSES AND SYSTEMS FOR COLLECTION, CRYOGENIC STORAGE AND DISTRIBUTION OF COSMETIC FORMULATIONS FROM AN OBTAINED STEM CELL BASED BIOLOGICAL MATERIAL

CROSS REFERENCE TO RELATED APPLICATIONS

This application claims priority to U.S. Provisional Application No. 61/468,132 filed Mar. 28, 2011, U.S. Provisional Application No. 61/582,026 filed Dec. 30, 2011, and U.S. Provisional Application No. 61/588,841 filed Jan. 20, 2012, each incorporated herein in their entirety.

FIELD OF THE INVENTION

The invention is directed to a business method for collection, cryogenic storage and distribution of cosmetic formulations from an obtained stem cell based biological sample material.

BACKGROUND OF THE INVENTION

The business of collecting, processing, and long term storage of biological samples allows healthy individuals to privately preserve their tissue for future use in therapy. Individualized collection and storage provides a solution to and for "personalized medicine" issues or as "bioinsurance" by making the patient's own preserved tissue available for future use.

Cosmetic products which are prepared using components which are known to actively address physiological pathways while simultaneously addressing basic dermatological issues are rapidly gaining scientific recognition and market share. Building business methods, processes and systems which support and advance this concept is recognizing the future of the intersection of science and cosmetics Business methods which are established for this reason are not only required to coordinate a unique process for the specific tissue for preservation, but also include equipment to complement the process to accomplish this objective. In addition, successful methods also need to appreciate and include other services to effectively and efficiently obtain a substantially pure and viable cryogenically stored sample for later use.

Recent developments in the understanding and properties of tissues and cells allow for advancement in science wherein biological samples obtained can be processed and cryogenically stored for later use for a variety of therapies. This is most appreciated in the use of heterologous and autologous stem cells and related growth factors and growth medium. However, though the science may exist, a cost effective, dependable and long-term business method must also exist to make this idea viable.

BRIEF SUMMARY OF THE INVENTION

In a first embodiment, the invention is directed to a business method for the processing and production of a stem cell based cosmetic. The method is initiated by designating a stem cell based biological material and thereafter, collecting a premium for defined services for collection, processing and transportation of the stem cell based biological material are established. The business method continues by obtaining the stem cell based biological material from a source and processing the stem cell based biological material to form at least one biological product for use in a cosmetic product. Testing the at least one biological product for quality control will be performed at least at the completion of the "processing" and prior to moving forward with producing any cosmetic product.

Upon quality control testing which will define the at least one biological product, a vehicle formulation is prepared for a particular cosmetic product desired. The at least one biological product is combined with the vehicle formulation for a particular cosmetic product to obtain a particular cosmetic product.

In another embodiment, the invention is directed to a system for producing a stem cell based cosmetic formulation product. The system includes a stem cell based biological material collection system and a stem cell based biological material transportation system for transporting the components of the stem cell based biological material collection system to a processing facility. The processing facility has a database which processes the stem cell based biological material to form at least one biological product. A storage facility stores the at least one biological product and a retrieval system is included for distributing the at least one biological product. A cosmetic formulation processing facility prepares a cosmetic formulation based on the at least one biological product.

In another embodiment, the invention is directed to a method for preparing an autologous cosmetic composition including the steps of obtaining a biological sample from a client and separating the biological sample to obtain a defined separation product. The defined separation product is combined with a growth media to obtain stem cells grown to confluence. The stem cells grown to confluence are combined with a non-growth media to obtain an active substance which is isolated. The isolated active substance is combined with a cosmetic formulation.

In another embodiment the invention is directed to a method of preparing components for a stem cell based cosmetic by ultrasonic cavitation including the steps of forming a stromal vascular fraction by ultrasonic cavitation of an adipose tissue sample and thereafter, combining the stromal vascular fraction with a growth media to grow stem cells to confluence. The stem cells are isolated and thereafter combined with a non-growth media allowing secretion of cytokines from the stem cell to produce an active substance, wherein the active substance is combined with a cosmetic formulation to form a cosmetic product.

In still another embodiment, the invention is directed to a method to prepare an ethnic stem cell based cosmetic product including the steps of obtaining a biological sample from a donor of a defined ethnicity and processing the biological sample to obtain an active substance. The active substance is combined with a cosmetic formulation.

In yet another embodiment the invention is directed to a business method for continuous supply of an ethnic stem cell based cosmetic product. The business method of the present embodiment is initiated by selecting a donor of a defined ethnicity and obtaining a biological sample from the donor of a defined ethnicity. Coordinating the processing of the biological sample, wherein the biological sample is disassociated to obtain a defined separation product and thereafter, processing the defined separation product forms an active substance. The active substance is combined with a cosmetic formulation that contains an active ingredient for a defined desired property of an ethnic group to form an ethnic stem cell based cosmetic product. The ethnic stem cell based cosmetic product is commercially distributed to consumers in various methods recognized in the industry.

DETAILED DESCRIPTION OF THE INVENTION

Figure 1:
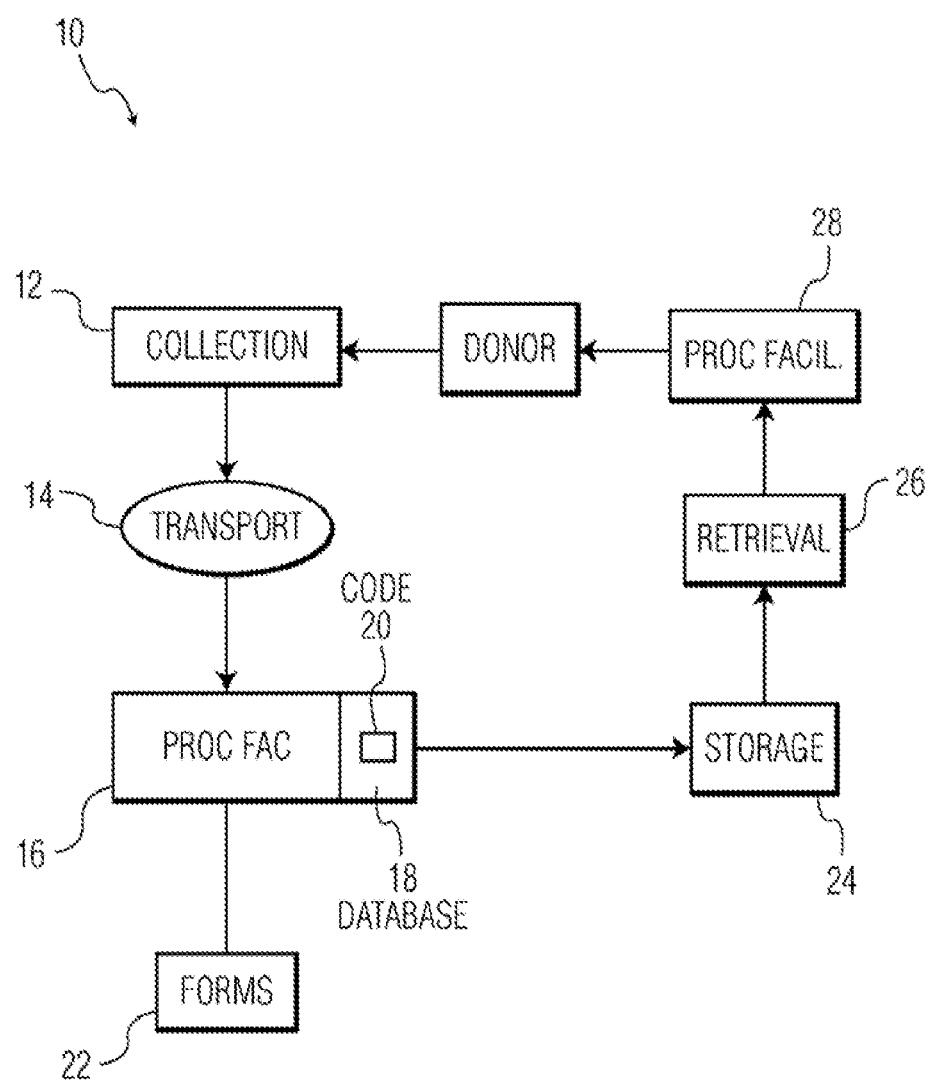
FIG. 1 is a schematic view of the system of the present invention.

Certain terminology is used herein for convenience only and is not to be taken as a limitation on the present invention. The terminology includes the words specifically mentioned, derivatives thereof and words of similar import. Certain terms such as "biological sample" and "biological material" can be used synonymously, as can "biological product", "isolated material" and "separation product" and also, "active substance" and "conditioned media".

The embodiments discussed herein are not intended to be exhaustive or to limit the invention to the precise form disclosed. These embodiments are chosen and described to best explain the principle of the invention and its application and practical use and to enable others skilled in the art to best utilize the invention.

In a first embodiment, the invention is directed to a business method for the processing and production of a stem cell based cosmetic. The method is initiated by designating a stem cell based biological material. The source of the stem cell based biological material could vary to include an autologous client, a homologous source or a commercially obtained composition, e.g. a medium composition which includes stem cells. The commercially obtained composition could be from a heterologous source, most commonly bovine.

Upon designation of the stem cell based biological material, collecting a premium for defined services for collection, transportation, and distribution of the stem cell based biological material is established. The particular collection protocols are defined, coordinated and implemented based on the services and source. Thus, the business method of the present invention includes defined premium collecting methods and information recordation designed for particular services based on the stem cell based biological material source (as discussed in detail in the examples herein).

The business method continues by obtaining the stem cell based biological material from a source as previously discussed. It will be appreciated that methods to obtain the stem cell based biological material will reflect standard medical services based on autologous, homologous or heterologous stem cells which form the basis of a cosmetic product.

Processing the stem cell based biological material to form at least one biological product for use in the cosmetic product is defined by the requirements of the stem cell based biological material and client information tracking, in addition to, and separate from, "digestion" protocols. One of skill in the art will recognize that various methods, manual, mechanical and/or chemical can be used for digestion. However, as previously discussed the particular process and information obtained will depend on the source of the stem cell based biological material. As will be appreciated by the examples herein, autologous samples obtained will require the greatest amount of information "tracking" in addition to the probability of the increased "digestion" steps. In contrast, commercially obtained (heterologous) materials will require the least amount of information tracking and "digestion".

Testing the biological products for quality control will be performed at least at the completion of the "processing" and prior to moving forward with producing any cosmetic product. All testing will be at a minimum as required by the United States Food and Drug Administration.

Upon quality control testing which will define the biological product, a vehicle formulation is prepared for the particular cosmetic product desired. The vehicle formulation will be based on 1) the "defined" biological product, and 2) the requirements of the particular cosmetic product desired. One of skill in the art will appreciate that a vehicle formulation for a "foot cream" will be very different from an "eye serum". The formulation will coordinate with information obtained from each step of the business method of the present invention to establish a formulation which will efficiently and effectively allow the expression of all the components of the biological product.

The biological product is combined with the vehicle formulation for the particular cosmetic product to obtain the particular cosmetic product desired. Core to this business method is establishing a method of combination which allows exponential benefits of the active ingredients and is cost effective based on the source of the stem cell based biological material.

The business method may further include coordinating a cosmetic procedure by a service provider using the particular cosmetic product. Important to the concept of the present invention is an appreciation of the continued relationship between a client and a service provider, most commonly a physician or trained technician. The continued relationship will allow the cosmetic formulation to be applied by the service provider during additional sessions and "check-ups". Coordinating the application of the particular cosmetic product with services, most commonly dermatological services such as peelings, facials etc., will allow the client the confidence that the particular cosmetic product is being used and applied correctly, and most importantly, most effectively. Having the opportunity to have the particular cosmetic product applied by a service provider in coordination with other treatments, when the particular cosmetic product can be most effective, will build the relationship between the client and service provider to allow a long term relationship to obtain the results the client desires.

The business method may include cryopreserving the at least one biological product so that once obtained it can be used for future cosmetic preparations and allows the same at least one biological product to be used for different "particular" cosmetic products. Thus, the business method can be repeated upon the quality control testing allowing re-ordering by a client to obtain a particular cosmetic product from the at least one biological product.

Various examples will now be described for explanation of the business method of the present invention; this is a non-limiting list of examples and should not be understood to illustrate all potential examples within this business method.

Example 1

Autologous Cryogenically Preserved Particular Cosmetic Product

Example 1 is directed to a business method for collection, cryogenic storage and distribution of an autologous biological sample material to prepare a particular cosmetic product. The method is initiated by collecting a premium for defined services for collection, cryogenic storage and distribution of a biological sample material and thereafter coordinating the collection of a biological sample of a customer by (i) paying a predetermined fee in support of physician services performed for collection of the biological sample and (ii) supplying a collection system including a plurality of components for collection and transportation of the biological sample. This initial part of the business method is important not only to obtain the sample but to initiate the business relationship of the customer and business entity. The customer, physician and business entity will gain an understanding of the "big picture" and long-term relationship of this collaboration so as to appreciate the benefits, rights, obligations and costs (as explained herein).

The pre-determined fee for a physician to obtain the biological sample could vary but will, mostly likely be limited to costs relating to the collection system and transportation to the processing facility. However, the cost will be a one-time set fee which will be agreed upon by the client before initiating the procedure to obtain the sample.

The collection system is a defined set of components which are designed for coordination of the business method. The collection system includes an identification material for the obtained biological sample. This is most commonly a defined group of standard forms which may include coded labels for use with an encoded program (as discussed herein). Client sample bags include the same coded labels for use with the encoded program. These labels will comply with state and federal regulations, e.g. 21 CFR 11. The collection system further includes a transportation box which may be commercially manufactured and coordinated with a transportation carrier, e.g. Biologics Box by FedEx. Transportation labeling will also include the same coded labels for use with the same encoded program; in addition to information regarding shipment location. Upon coordination, the method continues by obtaining the biological sample from the client and transporting the biological sample in the collection system to a processing facility.

At the process facility, the collection system components are introduced to a processing module of a database via a log-in port; having the encoded program. The database will be custom-designed to process and store "eProtected" health information using a commercially available program such as Microsoft's Access program. The database will include but is not limited to, the information obtained from the collection system to coordinate the "client sample with the client"; such as the information included in the patient-specific bar-coded client sample bags. This information will also be included in a standardized form. The database will be searchable and may be programmed to produce all the various forms associated with this process.

The autologous biological sample is processed by digestion to separate and isolate material. Isolating the biological sample and ensuring the quality of the biological sample is an imperative key to the commercial success of the method. Testing is performed for quality control of the isolated material for cryopreservation (if requested) and thereafter, the isolated material is cryopreserved in at least one aliquot and stored.

Upon request for use the isolated material is thawed in the at least one aliquot. The isolated material is then prepared into at least one cosmetic autologous formulation including the isolated material in the at least one aliquot.

The client can "re-order" from a cryopreserved sample as desired until the sample is exhausted. It will be appreciated that additional products can be obtained by repeating this process initiating with obtaining the autologous sample.

The business method further comprises coordinating a cosmetic procedure by a service provider using the at least one cosmetic autologous formulation. As discussed, core to the concept of the present invention is an appreciation of the continued relationship between a biological sample donor and a service provider, most commonly a physician or trained technician. The continued relationship will allow the cosmetic autologous formulation to be applied by the service provider during additional sessions and "check-ups".

The cosmetic autologous formulation is formulated for a defined section of the body, including but not limited to a face cream, foot cream or eye cream.

Most commonly, the obtained biological sample is an adipose tissue sample, wherein the isolated material in the form of a stem cell pellet consisting essentially of a mixture of pre-adipocytes, adipose-derived mesenchymal stem cells, microvascular endothelial cells, endothelial progenitor cells, and monocytes.

Example 2

Homologous Cryogenically Preserved Particular Cosmetic Product

Another example would include the steps of Example 1 for an autologous cryogenically preserved particular cosmetic product but using a homologous source rather than an autologous source. All of the other steps and concepts would remain the same recognizing the different properties which would exist by basing the product on a homologous instead of autologous stem cell source; including, but not limited to, the formulation prepared for combing with the biological sample.

Example 3

Heterologous Particular Cosmetic Product

In this example, the invention is directed to a business method for the processing and production of a stem cell based cosmetic. The method is initiated by designating a stem cell source from a heterogeneous source. The source of the stem cells is a commercially obtained composition, e.g. a medium composition which includes stem cells. The commercially obtained composition could be from a heterologous source, most commonly bovine.

A fee is collected to cover the costs of obtaining the commercial composition, processing, quality testing and preparation of the formulation and finally, preparation of particular cosmetic product.

The heterologous stem cell composition is obtained which form the basis cosmetic product.

Processing the composition to form at least one biological product for use in the cosmetic product includes requirements of stem cells sample and client information tracking in additions and separate from "digestion" protocols. Additionally, any process or digestion which is required by the manufacturer of the commercial product will be preformed based on the manufacturer instructions, if any. In any process, the commercial product will be digested so as to be acceptable for combination with a vehicle formulation. This includes cryopreservation procedures, if required. It will be appreciated that cryopreservation may not be required or desired.

Testing the biological products for quality control will be performed at least at the completion of the "processing" and prior to moving forward with producing any cosmetic product. All testing will be at a minimum as required by the United States Food and Drug Administration.

As in the previous examples, upon quality control testing which will define the biological product, a vehicle formulation is prepared for the particular cosmetic product desired. The vehicle formulation will be based on 1) the "defined" biological product, and 2) the requirements of the particular cosmetic product desired. One of skill in the art will appreciate that a vehicle formulation for a "foot cream" will be very different from an "eye serum". The formulation will coordinate with information obtained from each step of the business method of the present invention to establish a formulation which will efficiently and effectively allow the expression of all the components of the biological product.

As in the previous example, the biological product is combined with the vehicle formulation for the particular cosmetic product to obtain the particular cosmetic product. One of skill in the art will recognize that various methods, manual, mechanical and/or chemical can be used to combine the vehicle formulation and biological product. Core to this business method is establishing a method of combination which allows exponential benefits of the active ingredients and is cost effective based on the source of the stem cells.

As in the previous example, the business method may further include coordinating a cosmetic procedure by a service provider using the particular cosmetic product, as discussed herein.

Referring to FIG. 1, in another embodiment, the invention is directed to a system for producing a stem cell based cosmetic formulation product 10. The system 10 includes a stem cell based biological material collection system 12 and a stem cell based biological material transportation system 14 to a processing facility 16, having a database 18. The database 18 includes an encoded program 20 to organize and store information regarding the stem cell based biological material and recording information. This includes information on standardized forms 22 which can be used in various parts of the system 10.

The collection system 12 has been defined in the previous embodiments and is usually in a "fitted box" for ease in use. As discussed herein, the collection system transportation system 14 is usually in coordination with a commercial carrier, such as Fed Ex®, which has the ability to transport medical samples using specific equipment in compliance with local, state and federal regulations.

At the completion of the processing stem cell based biological material to form at least one biological product at the processing facility 16, the at least one biological product is located in a storage facility 24. This is commonly a "freezer" of a defined size, having the capability and construction to coordinate with a second (permanent) storage facility (not shown) such as Novare® Bio-Logistics. Potentially, a strategic partnership is formed within the business method of the current invention. It is understood that the processed at least one biological product does not require cryopreservation and can be immediately used to form the particular cosmetic product. Thus, the system 10 may not require a storage facility wherein no cryopreservation is required. In situations, wherein no cryopreservation is desired, the storage facility could be limited to an acceptable biological container at a preservation temperature.

At the occurrence of storage subscription renewal or a request for the cryogenically stored at least one biological product, the system 10 may include a retrieval system 26 for distributing the at least one biological product to multiple "end-user" opportunities (including the Donor as illustrated in FIG. 1).

Most commonly, the initial fees obtained are limited to the collection, digestion and initial storage of the stem cell based biological material and at least one biological product but does not include fees for the preparation of the cosmetic formulation.

A cosmetic formulation processing facility 28 prepares a cosmetic formulation based on the at least one biological product obtained. The cosmetic formulation processing facility 28 accepts the "thawed" isolated material or material which has not been cryopreserved. As discussed herein, the cosmetic formulation can be multiple products including but not limited to face, eye and/or foot creams or serum.

In another embodiment, the invention is directed to a method for preparing an autologous cosmetic composition including the steps of obtaining a biological sample from a client and separating the biological sample to obtain a defined separation product.

The defined separation product is combined with a growth media to obtain stem cells grown to confluence. The stem cells grown to confluence are combined with a non-growth media to obtain an active substance which is isolated. The isolated active substance is combined with a cosmetic formulation. The combination of the isolated active substance and the cosmetic formulation creates a desired cosmetic product.

Figure 2:
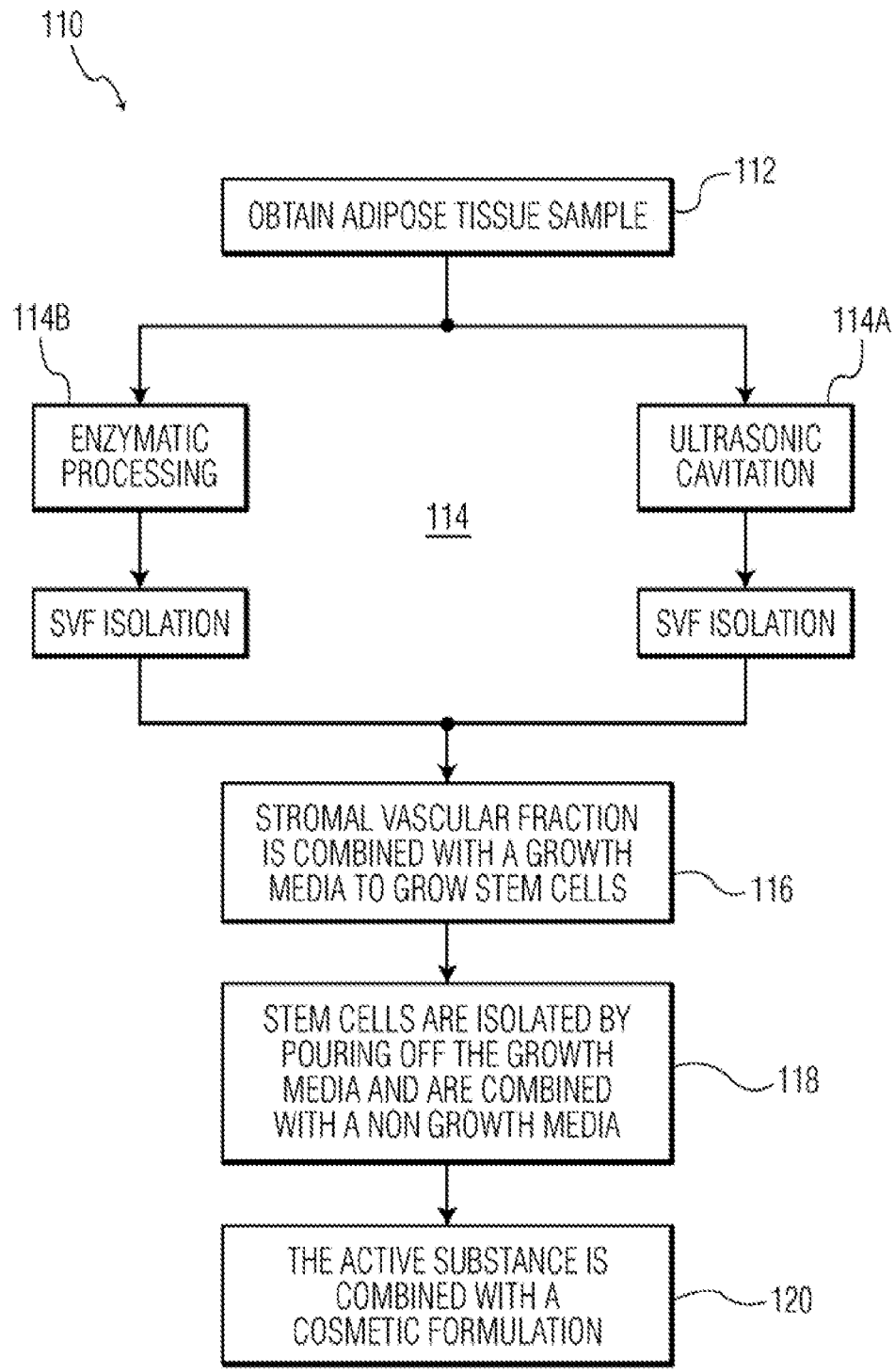
FIG. 2 is a flowchart illustrating the process of preparing a cosmetic product via two methods of separation, achieving a defined separation product to obtain an active substance for forming a cosmetic product.

Referring to FIG. 2, illustrating the present embodiment of the method 110, the biological sample is adipose tissue, obtained by aspiration 112; most commonly by a medical professional. However, one skilled in the art would recognize that the invention is not limited to adipose tissue but may be directed to other biological samples, e.g. platelet rich plasma (PRP).

The defined separation product in the present embodiment is a stromal vascular fraction (SVF); the portion of adipose tissue that supports growth. More particularly, SVF is the lipoaspirate obtained from liposuction minus the fat cells (adipocytes). Apart from adipocytes, the SVF contains a variety of other cells such as pre-adipocytes, endothelial cells, smooth muscle cells, pericytes, fibroblasts, and adult stem cells (ASCs). In addition, the SVF also contains blood cells from the capillaries supplying the fat cells. These include erythrocytes or red blood cells, B and T cells, macrophages, monocytes, mast cells, natural killer (NK) cells, hematopoietic stem cells and endothelial progenitor cells, to name a few. Furthermore, SVF, in addition to the adipocyte endocrine secretions, also contains growth factors such as transforming growth factor beta (TGF), platelet-derived growth factor (PDGF), and fibroblast growth factor (FGF), among others. This is consistent with the secretions of cells in the presence of an extracellular matrix. The SVF also contains the various proteins present in the adipose tissue.

Separation to obtain the defined separation product 114, e.g. SVF, can be achieved in a variety of methods as discussed herein. In one method 114A, separation of the adipose tissue can be achieved by ultrasonic cavitation, primarily associated with cell disruption (lysis) or disintegration. Generally, in describing ultrasonic cavitation, when sonicating liquids at high intensities, the sound waves that propagate into the liquid media result in alternating high-pressure (compression) and low-pressure (rarefaction) cycles, with rates depending on the frequency. During the low-pressure cycle, high-intensity ultrasonic waves create small vacuum bubbles or voids in the liquid. When the bubbles attain a volume at which they can no longer absorb energy, they collapse violently during a high-pressure cycle. This phenomenon is termed cavitation. During the implosion very high temperatures (approx. 5,000K) and pressures (approx. 2,000 atm) are reached locally. The implosion of the cavitation bubble also results in liquid jets of up to 280 m/s velocity. The resulting shear forces break the cell envelope mechanically and improve material transfer. Ultrasound can have either destructive or constructive effects to cells depending on the sonication parameters employed.

Alternatively, separation can be achieved by enzymatic digestion of the adipose tissue 114B, wherein chemical substances separate the cell to obtain the defined separation product.

The stromal vascular fraction is combined with a growth media to grow stem cells to confluence 116. The growth media can be of a variety of commercially available products having the composition to allow growth. However, specie specific media can be used which will eliminate any type immunological reaction, for example, the media described in U.S. Pat. No. 7,989,205. One of skill in the art would recognize this step of the process can be repeated to obtain a defined or required number of cells.

Upon growth to confluence, an enzyme, e.g. Tripson, can be added to digest the linkage from "the surface" of the container in which "growth occurred", wherein the stem cells "float" in the liquid media. The stem cells are isolated by pouring off the growth media and are combined with a non-growth media 118. The non-growth media, for example media limited to carbohydrates, is added to the container in which growth occurred. This allows secretion of cytokines from the stem cells into the "non-growth" media to produce the active substance.

Using either method described herein (or other separation methods which achieve a stromal vascular fraction) the active substance is combined with a cosmetic formulation 120 having (i) a ph of between 6.0 and 8.0, and (ii) contains no proteases and (iii) is sterile.

The present embodiment further appreciates including in the defined separation product and growth media combination, tropoelastin to form the active substance. Adding tropoelastin when combining the growth media and the stromal vascular fraction will add additional properties to the active substance.

An autologous cosmetic product is formed by the method having defined properties for multiple uses. The autologous cosmetic product achieved by the method of the present embodiment can serve multiple purposes including regenerative, anti-aging and beauty enhancement products but also to work with the body in multiple capacities to achieve designated ends. Such capacities would include a method for stimulating skin (dermis) cells by contacting the dermis of a living individual with an autologous cosmetic product of the present embodiment.

In another embodiment, the invention is directed to a method of preparing components for a stem cell based cosmetic by ultrasonic cavitation. Using ultrasonic cavitation in a defined method for preparation of a cosmetic, focuses the properties and advantages of this method for preparation of components to achieve a specific objective; components which have properties which will allow preparation of the cosmetic. Thus, in the present embodiment, ultrasonic cavitation is used to obtain components (via the separation activity) which "dovetail" with the other "steps" of the method for preparing an autologous cosmetic composition presented herein or related method for the same purpose.

Ultrasonication is an effective means to break cell structures. This effect can be used for the extraction of intracellular materials, e.g. starch from the cell matrix. Ultrasonication generates alternating high-pressure and low-pressure waves in the exposed liquid. During the low-pressure cycle, the ultrasonic waves create small vacuum bubbles in the liquid that collapse violently during a high-pressure cycle; termed "cavitation". The implosion of the cavitation bubble causes strong hydrodynamic shear-forces. The shear forces can disintegrate fibrous, cellulosic material into fine particles breaking the walls of the cell structure. This releases more of the intra-cellular material, such as starch or sugar into the liquid. In addition, the cell wall material is being broken into small debris. This effect can be used for fermentation, digestion and other conversion processes of organic matter. After milling and grinding, ultrasonication makes more of the intra-cellular material e.g. starch as well as the cell wall debris available to the enzymes that convert starch into sugars. More importantly to the present embodiment, ultrasonic cavitation increases the surface area exposed to the enzymes during liquefaction or saccharification.

In the present embodiment, the cell yield by ultrasonic cavitation requires a high concentration of serum for growth of the cells for use in obtaining a cosmetic product. Without recognition of this requirement, the yield of cell growth does not form a basis for use in a cosmetic product nor does it allow for a successful commercial method.

The method of the present embodiment includes the steps of forming a stromal vascular fraction by ultrasonic cavitation of an adipose tissue sample in a defined manner to achieve a successful defined separation product which can be used within a defined method for making a cosmetic product. Once the defined manner of use of ultrasonic cavitation is completed, the resultant stromal vascular fraction is combined with a growth media to grow stem cells to confluence. The stem cells are isolated and thereafter combined with a non-growth media allowing secretion of cytokines, and other growth materials, from the stem cell to produce an active substance, wherein the active substance is combined with a cosmetic formulation to form a cosmetic product.

As in the previous embodiment, the active substance is combined with a cosmetic formulation having (i) a ph of between 6.0 and 8.0, and (ii) contains no proteases and (iii) is sterile and further, the growth media is either a commercially available media or a specie specific media. Additionally, as in the previous embodiment, tropoelastin can be combined with the growth media and stromal vascular fraction in obtaining the active substance. The autologous cosmetic product formed by the method will have properties commensurate with components obtained by ultrasonic cavitation.

In still another embodiment, the invention is directed to a method to prepare an ethnic stem cell based cosmetic product including the steps of obtaining a biological sample from a donor of a defined ethnicity and processing the biological sample to obtain an active substance. The donor is most commonly a person having superior qualities in regard to physical appearance including facial features, muscular appearance and skin quality. The stem cell donor will exemplify the ethnic characteristic desired by consumers of cosmetic products. The active substance is combined with a cosmetic formulation.

The cosmetic formulation in the present embodiment contains an active ingredient for a defined desired property of an ethnic group. The formulation will be complementary to the active ingredient so as to allow a potential synergistic relationship but will also contain components which will have desired results of a particular ethnic group of the donor, e.g. a skin lightener.

Processing the biological sample includes separating the biological sample to obtain a defined separation product. As in the previous embodiments, the defined separation product is most commonly an SVF obtained as discussed herein and combined with a growth media to obtain stem cells grown to confluence. The stem cells grown to confluence are isolated and thereafter, combined with a non-growth media to obtain an active substance, which is isolated. The active substance is combined with a cosmetic formulation as described herein to form an ethnic stem cell based cosmetic.

Figure 3:
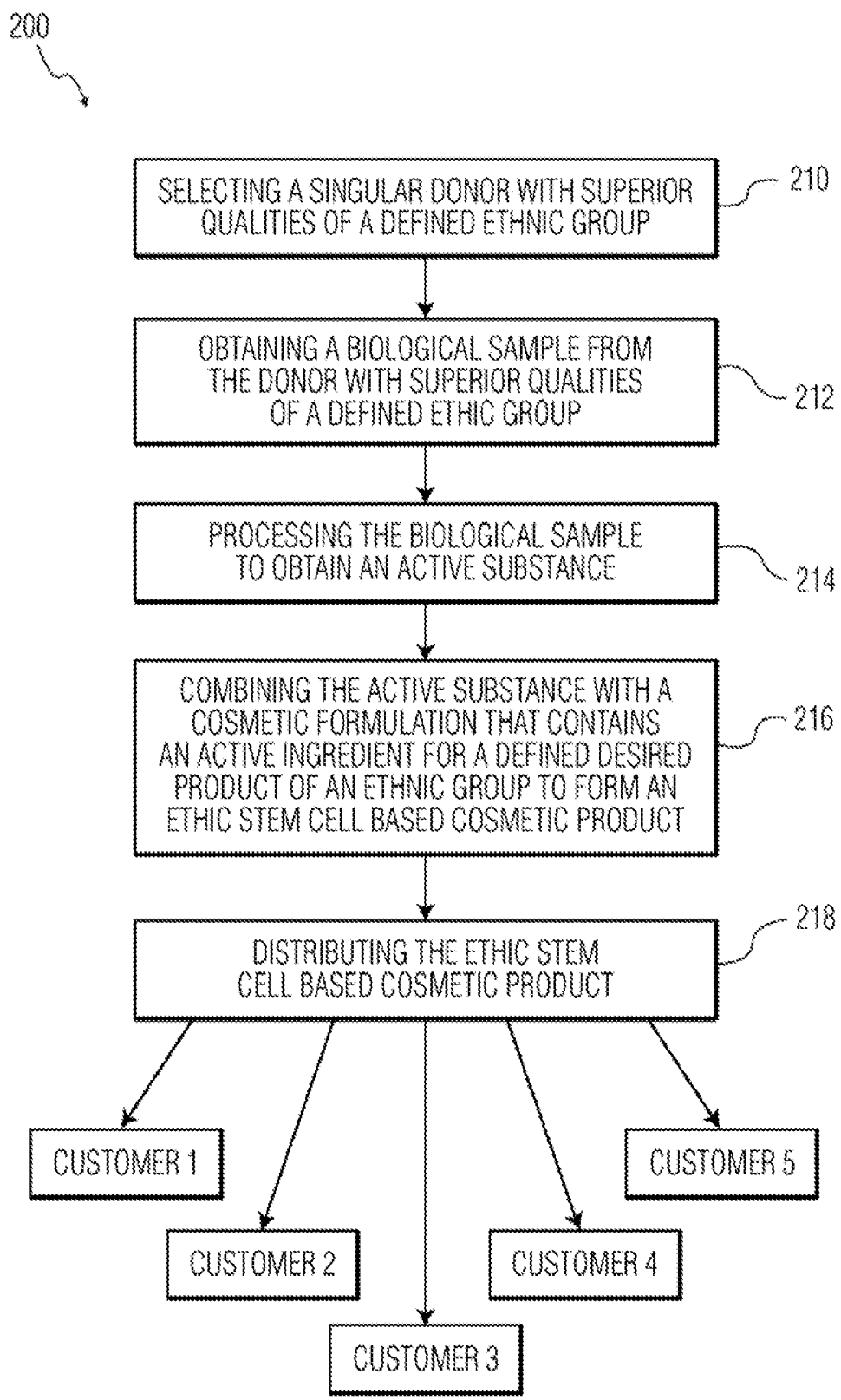
FIG. 3 is a flowchart illustrating the business method for continuous supply of an ethnic stem cell based cosmetic product.

Referring to FIG. 3, in yet another embodiment the invention is directed to a business method for continuous supply of an ethnic stem cell based cosmetic product 200. The business method of the present embodiment is initiated by selecting a donor of a defined ethnicity 210 and obtaining a biological sample from the donor of a defined ethnicity 212. As discussed in the previous embodiment, the donor selected will illustrate the desired characteristics associated with an ethnic group.

The processing of the biological sample is coordinated, wherein the biological sample is disassociated to obtain a defined separation product and thereafter processing the defined separation product forms an active substance 214. The coordination and processing can be achieved in defined manners which will contribute to the final consumer cosmetic product as discussed herein.

The active substance is combined with a cosmetic formulation that contains an active ingredient for a defined desired property of an ethnic group to form an ethnic stem cell based cosmetic product 216. The active ingredient and formulation will be selected so as to satisfy the desired properties of the ethnic stem cell based cosmetic product but also in a manner which is cost effective for commercial success. The ethnic stem cell based cosmetic product is commercially distributed to a plurality of customers in various methods recognized in the industry 218.

Example 4

Business Method and Preparation Method of an Autologous Adipose Tissue Stem Cell Based Cosmetic Product In the present example, the method is initiated by designating an autologous stem cell based biological material of adipose tissue from an adult male. Upon designation of the stem cell based biological material, a premium is collected for defined services for collection, transportation, processing and distribution of the stem cell based biological material. The particular collection protocols are defined, coordinated and implemented based on the services required.

In the present example, a shipment package including a defined client sample container is forwarded to the location of extraction of the biological sample. The "shipment package" or "collection system" includes various components in addition to the defined container with the client information for extraction of the client/adipose tissue sample by a physician. In an effort to increase the overall content of fat delivered by the physician, an additional 60 mL syringe was included to the collection system in this example. The instructions are amended to have the physician load both syringes with lipoaspirate, let stand 10 minutes then inject both into one collection bag of the collection system.

Inspecting the shipment package includes ensuring that (a) the defined client container is not past a defined expiration date, (b) the client sample was collected within the past 48 hours, and (c) the recording information is accurate. If the conditions of a, b, or c are not met, then the sample is not acceptable and must be discarded as biohazard waste. This discard will be recorded for organization and "tracking" of the sample.

Most commonly, the shipment package includes a bar-coded, medium-filled client sample container in an outer container (as discussed herein), a sterile, 60 mL syringe, a patient-specific bar-coded shipping container approved for biohazardous materials containing an absorbent sheet, a Tyvek® outer container, sufficient bubble-wrap to stabilize the contents, and foam insulation in an outer corrugated cardboard box (the latter items commercially available from Saf-T-Pak®). The appropriate needles/cannula and other medical supplies are generally accessible equipment which will be supplied by the physician, but may be included as part of the shipment.

The method continues by introducing the shipment package components to a processing module of a database via a log-in port by scanning a barcode on the client sample container in the completed recording information. The database is custom-designed to have the ability to comply with the requirements of the American Association of Blood Banks (AABB) standard 6.3 and 21 CFR § 820.30 (FDA Guidance, Jan. 11, 2002, "General Principles of Software Validation) using, for example, a commercially available program such as Microsoft's Access program. The database includes (but is not limited to), the information obtained from the shipment package to coordinate the client sample with the client; such as the information included in the patient-specific bar-coded shipping container. This information will also be included in a standardized form. The database will be organized in modules similar to the organization in the standardized form, will be searchable, and will be programmed to produce all the various forms associated with this process.

At the establishment of an acceptable client sample, one vial each of collagenase, neutral protease, and DNase I is removed from a freezer and thawed in a biosafety cabinet for use in a digestion solution. In the present example, a pre-defined mixture of collagenase and neutral protease was used, Roche Liberase®, which contains both collagenase I and collagenase II, plus thermolysin, a neutral protease. Thawing at room temperature and without assistance supports in the protection of the integrity and viability of these solutions.

The client sample was removed from the outer shipping container and gently agitated in the client sample container manually to re-suspend the fat and any sediment in the medium, and further, to ensure that the sterility test samples will be representative of the contents. The sample container is wiped with alcohol from spray bottles with filter-sterilized 70% ethanol or iso-propanol to ensure it is not contaminated.

The client sample container is elevated or "hung" and allowed to stand undisturbed for approximately five (5) minutes to note the presence of visible blood and estimate the amount of oil from lysed fat as a fraction of the total adipose tissue present in the client sample. This observation is recorded in a defined manner on a pre-designed form. Observations such as the amount of oil present will be entered into a standardized form, and thus the information becomes part of the database. The bar codes on the containers will be scanned, and the information in the barcode will be imported into the database.

Sterility of the adipose tissue sample within the client sample container is tested to ensure the quality. The removal, via a bottom port of the client sample container, allows extraction by gravitational force thus eliminating any need for a "pump" etc. Sterility and microbial testing is performed by standard commercial systems such as BacT/Alert or similar testing. Specific testing procedures are performed in order to comply with and receive required AABB or other professional organization certification and adhere to specific current and future FDA rules as applicable. Sterility samples are kept at room temperature until sent to the contamination testing laboratory.

The adipose tissue sample is washed by disinfecting one of the top ports of the client sample container, by wiping with 70% or sterile alcohol with a swab, and adding a defined amount of salt solution. The defined amount is at least equal to the volume of adipose tissue sample to wash it effectively. The salt solution, e.g. Hank's Balanced Salt Solution (HBSS), is added by using a 60 cc syringe with an 18 gauge needle.

The client sample container is gently agitated and allowed to stand undisturbed for a defined time period; about five minutes. Using the same port that was used to obtain the sterility sample, the wash is removed and discarded. The container was allowed to "hang" in an elevated position undisturbed until fat is observed floating in a single layer at the top of the container. Oil dispersed from the adipose tissue sample is removed.

The digestion solution prepared is injected into the client sample container having the client/adipose tissue sample to form a digestion mixture within the client sample container. The outside of the vials of the digestion solution (thawed as previously discussed for use herein), was wiped to ensure sterility with an alcohol swab.

Using a sterile 2 ml pipette, the solution is transferred to a 50 mL centrifuge tube containing 48 mL HBSS pre-warmed to 37° Celsius. The tube was capped and mixed by gentle agitation. The basis of this dilution ratio is the concentration and enzymatic activity of the enzyme stock solutions, which are based on (i.) product protocols (ii.) experience, and (iii.) what is known in the art. The method of the instant application eliminates this variable by basing the enzyme dilution on the specific activity rather than mass, making the process more reproducible; critical for a commercial process.

The digestion solution is injected into the washed adipose tissue sample using one of the top ports of the client sample container. The digestion mixture is incubated at 37 degrees Celsius for 45 minutes while being agitated on a rocking platform at 24 rocks per minute. At the end of the digestion, the adipose tissue is converted from a suspension of tissue fragments up to 4 millimeters in size into a much smoother suspension in which most tissue fragments are less than 1 millimeter in diameter, as most of the adipose tissue is dissociated into isolated mature adipocytes and stromal-vascular fraction cells, although some whitish, connective tissue may remain intact. Thereafter, the solution is centrifuged at a low speed to separate the mature adipocytes from the rest of the digestion mixture.

The stromal vascular fraction ("SVF") phase of the centrifuged digestion mixture is withdrawn through a sterile, 40 micrometer mesh filter. The centrifugation of the digestion mixture in the client sample container serves to separate the SVF from the adipocytes and undigested adipose tissue. Removing this SVF from the client sample container to a centrifuge tube and re-centrifuging allows formation of a "tight" pellet at the bottom of the tube (as discussed herein), so that greater than 95 percent, and as much as 99 percent, of the enzyme solution can be removed.

The suspension of the filtered digestion mixture is centrifuged in two 50 mL tubes upon removal from the client sample container, isolating a "first" stromal vascular pellet. The supernatant of the centrifuged filtered suspension is removed. The stromal vascular "tight" first pellet is re-suspended by trituration in a red blood cell lysis buffer, eliminating red blood cells, as well as removing residual enzymes and debris, forming a cell suspension which is centrifuged to form a "second" pellet. The supernatant of the centrifuged cell suspension is removed.

The second pellet is re-suspended by titration adding HBSS forming a "second cell suspension". This second cell suspension is counted and analyzed for viability by using a small aliquot (20 micro liters) of the second cell suspension mixed with an equal volume of a mixture of acridine orange and propidium iodide stains and counted using the Nexcelom Cellometer Vision instrument (Nexcelom Biosciences). The second cell suspension is centrifuged to form a "third" pellet which is stored in a biosafety cabinet for further processing.

The "third pellet" defines a stem cell pellet product, e.g. a washed SVF pellet which includes a mixture of cells of pre-adipocytes, adipose-derived mesenchymal stem cells, microvascular endothelial cells, endothelial progenitor cells, monocytes, and small numbers of vascular smooth muscle cells. The mixture must contain no mature adipocytes, and at least 1% of the nucleated cells in the mixture must be adipose-derived mesenchymal stem cells. The mixture or "stem cell pellet product" or "washed SVF pellet" must exhibit a combined viability by acridine orange/propidium iodide or trypan blue dye-exclusion assay of no less than 35%. Further, the adipose-derived mesenchymal stem cells contained therein must be capable of proliferation when placed in contact with a suitable culture medium under appropriate environmental conditions known to those skilled in the art of cell culture.

Plate a T25 culture flask with a minimum of $1.0 \times 10^{06}$ SVF ("third pellet") for shipment to cosmetic product processing facility ("CCPF") plus one additional flask to create backup "PI" for storage in designated storage facility. Plating for the cosmetic product processing facility flask should be on a scale relative to overall SVF Yield as follows:

| SVF Yield | CCPF Flask | Primary Fac. Flask | Storage (SVF) |
| --- | --- | --- | --- |
| Below 2 Million | 1 million | 1 million | none |
| 2 million to 3.5 million | 1 million | 1 million | Balance 1 to 2 vials (QC |
| 3.5 Million to 5 million | 1.5 million | 1 million | Balance 2 to 4 vials (1 QC) |
| Above 5 million Cells | 2.0 million | 1.5 million | Balance 2 to 4 vials (min 1 QC) |

Flasks are coated with human plasma Fibronectin at ⁻1.5 p.g/cm². Culture is grown with 10 μg/ml of Gentamicin until BacT results show "negative" to ensure contamination is not present.

Forms are created for organization and storage of information regarding growth, etc. of the culture. The proprietary culture forms are designed to allow the direct flow of information into a computer system/database (as discussed herein). Specifically, the culture forms include labels that are proprietary and include (but are not limited to) a Client Number (barcoded) and Collection Date (barcoded). The information on the forms is transferred to an electron format, in this example, Microsoft Excel®, and thereafter transferred to a data standard for inclusion into a database. Therefore the information is accessible to both the primary facility and the cosmetic product processing facility.

The T25 culture flask with a minimum of $1.0 \times 10^6$ SVF for shipment to cosmetic product processing facility include a medium 0.5% FBS adipose stem cell medium with 10 µg/mL Gentamicin as described. A complete change of medium 18-24 hours after initial plating and "½ feeding" until appreciative growth of ASC's (adult stem cell's) have been established by visual inspection. One skilled in the art will appreciate ½ feed is generally defined as removal of about half the volume of spent medium from flask, then add equal or a little more fresh medium. In the present example, complete medium changes are performed prior to the weekend to ensure nutrient availability for cell viability and growth.

Upon recognition that the T25 culture flask is about 30% to 50% confluent, it is shipped to the cosmetic product processing facility (CPPF). To maintain viability of cells, the cells are sent overnight. It is recognized the SVF should not be sent on Friday or the day before a holiday. A copy of the culture record, original processing request, and 6 barcoded labels are included with the shipment to the cosmetic product processing facility. To ensure viability of the culture, it should be shipped in 13 to 15 days from the date of plating. Failure to ship within this time period will require review by a supervisor, management and cosmetic product processing facility. As will be appreciated, the system as described herein will alert laboratory staff of any delayed shipment to ensure the quality and viability of the culture.

Upon receipt at the cosmetic product processing facility, (13 to 15 Days post processing) the T25 Flask is "checked in" via the system "connected" to the system at the primary facility. The media in the received T25 Flask is reduced 80 to 90 percent upon receipt and incubated for 1 to 3 days until confluence.

The contents of the T25 Flask is plated into four (4) T75 flasks coated with human plasma Fibronectin using all recovered cells (a minimum of 300,000 cells per T75 flask). In the present example, no cells will be set aside for storage at this recovery. The T75 Flasks are placed in incubator and fed every 24 to 48 hours as necessary until greater than 80% confluent exists in each flask.

At 19 to 24 days post processing, and greater than 80% confluence, the growth media is replaced with non-growth media, HAM's F-12. One skilled in the art would recognize the non-growth media can be limited to a combination of sugars and carbohydrates. The T75 Flasks are incubated for 4 to 7 days allowing secretion of substances, e.g. cytokines, growth factors and proteins, into the non-growth media to create a "conditioned media".

Table 1 and replication Tables 1A and 1B, illustrate components of a conditioned media created by the method of the present example. Various assays illustrate levels of substances found in the conditioned media using various cell growth medium.

TABLE 1

Average Analyte Concentration, pg/ml

| | AG ID | | |
|---|---|---|---|
| | 1 | 2 | 3 |
| Sample Label Details | CCH1 p1 culture, ACC media | CCH2 p2 culture, ACC media | CCH3 p2 culture, MC media |
| EGF | 8.5 | <2.7 | 5.1 |
| Eotaxin | <2.2 | <2.2 | <2.2 |
| FGF-basic | <2.1 | <2.1 | <2.1 |
| Flt-3L | <3.1 | <3.1 | <3.1 |
| Fractalkine | 62.8 | 103.6 | 77.5 |
| G-CSF | 11.7 | 23.8 | <0.9 |
| GM-CSF | <5.7 | <5.7 | <5.7 |
| GRO | 695.0 | 693.4 | 17.7 |
| IFN-a2 | <10.2 | <10.2 | <10.2 |
| IFN-g | <0.3 | <0.3 | <0.3 |
| IL-1a | <2.3 | <2.3 | <2.3 |
| IL-1b | <0.7 | <0.7 | <0.7 |
| IL-1ra | <2.9 | <2.9 | <2.9 |
| IL-2 | <0.3 | <0.3 | <0.3 |
| IL-3 | <2.1 | <2.1 | <2.1 |
| IL-4 | <0.6 | <0.6 | <0.6 |
| IL-6 | 34.0 | 2.3 | 8.7 |
| IL-5 | <0.1 | <0.1 | <0.1 |
| IL-7 | 2.7 | 4.5 | <1.8 |
| IL-8 | 222.8 | 339.2 | 22.6 |
| IL-9 | <0.7 | <0.7 | <0.7 |
| IL-10 | 0.4 | <0.3 | 0.6 |
| IL-12p40 | <2.5 | <2.5 | <2.5 |
| IL-12p70 | <0.4 | <0.4 | <0.4 |
| IL-13 | <0.3 | <0.3 | <0.3 |
| IL-15 | <0.5 | <0.5 | <0.5 |
| IL-17 | <0.2 | <0.2 | <0.2 |
| IP-10 | 7.6 | 6.1 | 8.3 |
| MCP-1 | 946.1 | 562.8 | 201.1 |
| MCP-3 | 18.4 | 21.3 | <2.0 |
| MDC | <3.7 | <3.7 | <3.7 |
| MIP-1a | 15.2 | <3.5 | <3.5 |
| MIP-1b | 21.7 | <4.5 | <4.5 |
| PDGF-AA | 5.4 | 2.4 | 4.3 |
| PDGF-AB/BB | 13.6 | 21.7 | 2.1 |
| Rantes | 3.2 | <1.0 | 1.8 |
| sCD40L | <4.4 | <4.4 | <4.4 |
| sIL-2Ra | <4.3 | <4.3 | <4.3 |
| TGF-a | <0.3 | <0.3 | <0.3 |
| TNF-a | <0.4 | <0.4 | <0.4 |
| TNF-b | <1.8 | <1.8 | <1.8 |
| VEGF | 107.5 | 135.5 | 91.9 |

TABLE 1A

| | AG ID | | |
|---|---|---|---|
| | 1 | 2 | 3 |
| Sample Label Details | CCH1 p1 culture, ACC media | CCH2 p2 culture, ACC media | CCH3 p2 culture, MC media |
| EGF | 8.2 | <2.7 | 4.9 |
| Eotaxin | <2.2 | <2.2 | <2.2 |
| FGF-basic | <2.1 | <2.1 | <2.1 |
| Flt-3L | <3.1 | <3.1 | <3.1 |
| Fractalkine | 57.6 | 94.8 | 70.8 |
| G-CSF | 10.7 | 21.6 | <0.9 |
| GM-CSF | <5.7 | <5.7 | <5.7 |
| GRO | 724.7 | 721.6 | 18.4 |
| IFN-a2 | <10.2 | <10.2 | <10.2 |
| IFN-g | <0.3 | <0.3 | <0.3 |
| IL-1a | <2.3 | <2.3 | <2.3 |
| IL-1b | <0.7 | <0.7 | <0.7 |
| IL-1ra | <2.9 | <2.9 | <2.9 |
| IL-2 | <0.3 | <0.3 | <0.3 |
| IL-3 | <2.1 | <2.1 | <2.1 |
| IL-4 | <0.6 | <0.6 | <0.6 |

TABLE 1A-continued

| | AG ID | | |
|---|---|---|---|
| | 1 | 2 | 3 |
| IL-6 | 29.5 | 2.0 | 7.5 |
| IL-5 | <0.1 | <0.1 | <0.1 |
| IL-7 | 2.4 | 4.1 | <1.8 |
| IL-8 | 211.3 | 321.0 | 21.4 |
| IL-9 | <0.7 | <0.7 | <0.7 |
| IL-10 | 0.4 | <0.3 | 0.6 |
| IL-12p40 | <2.5 | <2.5 | <2.5 |
| IL-12p70 | <0.4 | <0.4 | <0.4 |
| IL-13 | <0.3 | <0.3 | <0.3 |
| IL-15 | <0.5 | <0.5 | <0.5 |
| IL-17 | <0.2 | <0.2 | <0.2 |
| IP-10 | 8.2 | 6.5 | 8.9 |
| MCP-1 | 896.6 | 524.8 | 184.5 |
| MCP-3 | 16.8 | 19.3 | <2.0 |
| MDC | <3.7 | <3.7 | <3.7 |
| MIP-1a | 14.8 | <3.5 | <3.5 |
| MIP-1b | 19.0 | <4.5 | <4.5 |
| PDGF-AA | 4.8 | 2.1 | 3.7 |
| PDGF-AB/BB | 13.1 | 20.7 | 2.0 |
| Rantes | 3.2 | <1.0 | 1.7 |
| sCD40L | <4.4 | <4.4 | <4.4 |
| sIL-2Ra | <4.3 | <4.3 | <4.3 |
| TGF-a | <0.3 | <0.3 | <0.3 |
| TNF-a | <0.4 | <0.4 | <0.4 |
| TNF-b | <1.8 | <1.8 | <1.8 |
| VEGF | 111.9 | 147.1 | 104.2 |

TABLE 1B

| | AG ID | | |
|---|---|---|---|
| | 1 | 2 | 3 |
| Sample Label | CCH1 | CCH2 | CCH3 |
| Details | p1 culture, ACC media | p2 culture, ACC media | p2 culture, MC media |
| EGF | 8.8 | <2.7 | 5.3 |
| Eotaxin | <2.2 | <2.2 | <2.2 |
| FGF-basic | <2.1 | <2.1 | <2.1 |
| Flt-3L | <3.1 | <3.1 | <3.1 |
| Fractalkine | 68.0 | 112.4 | 84.2 |
| G-CSF | 12.8 | 26.1 | <0.9 |
| GM-CSF | <5.7 | <5.7 | <5.7 |
| GRO | 665.2 | 665.2 | 17.1 |
| IFN-a2 | <10.2 | <10.2 | <10.2 |
| IFN-g | <0.3 | <0.3 | <0.3 |
| IL-1a | <2.3 | <2.3 | <2.3 |
| IL-1b | <0.7 | <0.7 | <0.7 |
| IL-1ra | <2.9 | <2.9 | <2.9 |
| IL-2 | <0.3 | <0.3 | <0.3 |
| IL-3 | <2.1 | <2.1 | <2.1 |
| IL-4 | <0.6 | <0.6 | <0.6 |
| IL-6 | 38.4 | 2.6 | 9.9 |
| IL-5 | <0.1 | <0.1 | <0.1 |
| IL-7 | 2.9 | 5.0 | <1.8 |
| IL-8 | 234.4 | 357.4 | 23.9 |
| IL-9 | <0.7 | <0.7 | <0.7 |
| IL-10 | 0.4 | <0.3 | 0.6 |
| IL-12p40 | <2.5 | <2.5 | <2.5 |
| IL-12p70 | <0.4 | <0.4 | <0.4 |
| IL-13 | <0.3 | <0.3 | <0.3 |
| IL-15 | <0.5 | <0.5 | <0.5 |
| IL-17 | <0.2 | <0.2 | <0.2 |
| IP-10 | 7.0 | 5.8 | 7.7 |
| MCP-1 | 995.6 | 600.8 | 217.7 |
| MCP-3 | 20.0 | 23.4 | <2.0 |
| MDC | <3.7 | <3.7 | <3.7 |
| MIP-1a | 15.6 | <3.5 | <3.5 |
| MIP-1b | 24.4 | <4.5 | <4.5 |
| PDGF-AA | 6.0 | 2.7 | 4.9 |
| PDGF-AB/BB | 14.1 | 22.7 | 2.2 |
| Rantes | 3.2 | <1.0 | 1.9 |
| sCD40L | <4.4 | <4.4 | <4.4 |

TABLE 1B-continued

| | AG ID | | |
|---|---|---|---|
| | 1 | 2 | 3 |
| sIL-2Ra | <4.3 | <4.3 | <4.3 |
| TGF-a | <0.3 | <0.3 | <0.3 |
| TNF-a | <0.4 | <0.4 | <0.4 |
| TNF-b | <1.8 | <1.8 | <1.8 |
| VEGF | 103.0 | 123.8 | 79.7 |

The conditioned media is harvested as appropriate and combined with a formulation created recognizing 1) a use for a particular product, e.g. a face cream, eye cream, skin cream, toner, hair product, serum and/or moisturizer, and 2) appreciating the properties (biological, physical and chemical) of the conditioned media to establish quality as well as effectiveness in use; or "elegance" as recognized by one skilled in the art of blending. In the present example, Table 2 is the formulation for a serum product. Table 3 is the formulation to form an eye cream product and Table 4 is the formulation used in a moisturizer product. Each cosmetic formulation has (i) a ph of between 6.0 and 8.0, and (ii) contains no proteases and (iii) is sterile and further, the growth media is either a commercially available media or a specie specific media.

TABLE 2

| Serum |
|---|
| Water |
| Carbomer |
| Adipose Derived Stem Cell Conditioned Medium |
| Hyaluronic acid |
| Glycerin |
| *Macrocystis Pyrifera* Extract, Hydrolyzed Wheat Protein (and) PVP (Skin Tightener - ST) |
| Dimethicone |
| Sodium Benzoate |
| Methyl Diisopropyl Propionamide (and) Ethyl Menthane Carboxamide (and) Menthyl Lactate (and) Lauryl Laurate (and) and *Zea Mays* (Corn) Starch (and) Hydrolyzed Corn Starch (and) Hydrolyzed Corn Starch Octenylsuccinate (SalCool) |
| Alpha-Arbutin |
| Tropoelastin |
| Fragrance |

TABLE 3

| Eye Cream |
|---|
| Water |
| Adipose Derived StemCell Conditioned Medium |
| *Carthamus Tinctorius* (Safflower) Seed Oil |
| Propylene Glycol |
| Isopropyl Palmitate |
| Glyceryl Stearate |
| PEG-100 Stearate |
| Carbomer |
| Palmitoyl pentapeptide-4 (Matrixyl) |
| Acetyl Hexapaeptide-8 (Argireline) |
| Hyaluronic acid |
| Tocopheryl acetate |
| Green Tea Extract |
| Caffeine |
| Haloxyl |
| *Macrocystis Pyrifera* Extract, Hydrolyzed Wheat Protein (and) PVP (Skin Tightener ST) |

TABLE 3-continued

Eye Cream

Provitamin B
Tropoelastin
Cetearyl Alcohol
Stearic Acid
Myristyl Myristate
Dimethicone
Triethanolamine
Sodium Benzoate
DMDM Hydantoin
Iodopropynyl Butylcarbamate
Tetrasodium EDTA
Fragrance

TABLE 4

Moisturizer

Water (Aqua)
*Carthamus Tinctorius* (Safflower) Seed Oil
Sodium Hyaluronate
Adipose Derived Stem Cell Conditioned Medium
Glycerin
Butylene glycol (and) Polysorbate 20 (and) Palmitoyl Pentapeptide-4 (Matrixyl)
Glyceryl Stearate (and) PEG 100 Stearate
Acetyl hexapeptide (Argireline)
Carbomer
Isopropyl Palmitate
Propylene Glycol
Tocopheryl Acetate
Tropoelastin
Cetearyl Alcohol (and) Ceteareth-20
Provitamin B 5
Stearic Acid
Triethanolamine
Sodium Benzoate
Disodium EDTA
Myristyl Myristate
Iodopropynyl Butylcarbamate
Dimethicone
Fragrance Referring to TABLES 1, 1A and 1B, each formulation in the present example is designed, based on the principles discussed herein. Specifically, to complement the amount of IL-8 achieved by the process of the present example, and specifically, the "ACC" media, the percentages of the "ingredients" in the formulation would be based on the amount of components, cytokines, proteins and growth factors, as illustrated by TABLES 1, 1A and 1B found in the "conditioned media". The ACC media, which is the subject matter of U.S. Pat. No. 7,989,205 (American Cryostem Corporation) correlates to an increased product of IL-8 compared to conditioned media obtained by use of the "MC" media product; MesenCult®.

The desired elegance of the cosmetic product will include properties such as consistency which will prohibit "running" or "dripping" of the product. For example, thickeners such as carbomers, hyaluronic acid, glycerol, and dimethicone can be used. Another property required is the ability to maintain shelf life of a product for commercial purposes. One skilled in the art would recognize that refrigeration may be required and is acceptable based on the product formulation for a particular product. One skilled in the art would recognize that the ability to have a synergistic effect of the components (including essential cytokines) based a defined formulation would be extremely advantageous for both biological properties of the particular product and commercial brand.

The T25 flask for subculture at the primary facility; 19 to 24 days post processing has an objective to ultimately freeze 5 to 10 P1 vials with a minimum of 1 million cells each for retrieval by the cosmetic product processing facility for future products. Priority is to plate 2 T75 flasks as follows:

| Primary Yield | P1 Flask −1 | P1 Flask −2 | Storage (PO) |
| --- | --- | --- | --- |
| Below 2 Million | 50% of cells | 50% of cells | none |
| 2 million to 3.5 million | 1 million | 1 million | Balance 1 to 2 vials (QC optional) |
| 3.5 Million to 5 million | 1 million | 1 million | Balance 2 to 4 vials (1 QC) |
| Above 5 million Cells | 1.5 Million | 1.5 million | Balance 2 to 4 vials (min 1 QC) |

Cells are plated in 0.5% FBS ASC Medium with 101.1. g/mL Gentamicin which will be removed at the first feeding. If BacT results are negative prior to this, it will be removed immediately. About 2 days prior to expected harvesting while cells are actively growing, feed with 2% HSA Medium.

At the primary facility, the P1 vials of adipose stem cells are cryopreserved. TrypLE™ is used to dissociate attachment-dependent mammalian cell lines both in serum and in serum-free conditions, and is substituted for trypsin. According to count, cryopreserve=count/1,000,000 (minimum 5 vials); 2 QC vials with $^-5 \times 10^5$ ASC (if available). Collect and test the supernatant using the BacT. Calculate the change in population doubling (ΔPD) from the plating at P1 to the P1 freeze:

$$Log_{10} [Yield/Seed] \times 3.3$$

Harvest the cells.

One of skill in the art would recognize quality control recovery is preferable. Specifically, in the current example, recover 1 quality control vial. Perform BacT test on ½ of the final cell suspension after cell count is removed and plate 1 T25 or T12.5 flask (according to count) coated with Fibronectin using 0.5% FBS ASC Medium. Subculture 2 times after recovery seeding each new flask with $1 \times 10^4$ ASC and harvest for count only after second subculture. If culture is not ready for subculture (or harvest) 14 days after plating, subculture is still performed. If the culture did not perform a complete population doubling, it is considered dead and has failed growth QC standard. If the culture did double, then continue with the QC process. Calculate the change in population doubling (APD), and the cumulative population doubling level (cPDL). Do not forget to include the cPDL from the P1 freeze:

$$\Delta PD = Log_{ie}[Yield/Seed] \times 3.32$$

$$cPDL = \Sigma APD$$

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for preparing an autologous cosmetic composition comprising the steps of:
   a. obtaining an adipose tissue sample from a client;
   b. separating the adipose tissue to form a stromal vascular fraction (SVF) wherein the SVF:
   (i) comprises a mixture of cells of pre-adipocytes, adipose-derived mesenchymal stem cells which are capable of proliferation, microvascular endothelial cells, endothelial progenitor cells, monocytes, and vascular smooth muscle cells,
   (ii) contains no mature adipocytes; and
   (iii) at least 1% of the nucleated cells in the SVF are adipose-derived mesenchymal stem cell (ADMSC);
   c. combining the SVF with growth media to grow the ADSMC to confluence;
   d. isolating the ADSMC grown to confluence;
   e. incubating the ADMSC in a non growth media to allow secretion of the active substances,
   wherein the active substance contains an amount of IL-8 in a concentration of about 230 pg/ml to 360 pg/ml;
   f. isolating the active substance; and
   g. combining the isolated active substances with a cosmetic formulation;
   wherein the cosmetic formulation has (i) a ph of between 6.0 and 8.0, (ii) contains no proteases, (iii) is sterile and (iv), comprises components based on the amount of cytokines, proteins and growth factors in the active substance.

2. The method of claim 1, wherein the tissue sample in step a. is extracted by aspiration.

3. The method of claim 2, wherein separation of the adipose tissue in step b. is achieved by enzymatic digestion.

4. The method of claim 3, wherein the combining of the SVF with a growth media in step c. further comprises combining tropoelastin with the SVF and growth media.

* * * * *